United States Patent
Xu et al.

(10) Patent No.: US 10,682,073 B2
(45) Date of Patent: Jun. 16, 2020

(54) MEASUREMENT DEVICE AND METHOD FOR HUMAN RESPIRATORY SYSTEM FUNCTION

(71) Applicant: Goldver Tech Systems Co. Ltd, Chupei, Hsin Chu County (TW)

(72) Inventors: Mengbiao Xu, Jiangsu (CN); Yonglong Xu, Jiangsu (CN)

(73) Assignee: Golver Tech Systems Co. Ltd, Chupei (TW)

(*) Notice: Subject to any disclaimer, the term of this patent is extended or adjusted under 35 U.S.C. 154(b) by 348 days.

(21) Appl. No.: 15/529,591

(22) PCT Filed: Nov. 25, 2014

(86) PCT No.: PCT/CN2014/092097
§ 371 (c)(1),
(2) Date: May 25, 2017

(87) PCT Pub. No.: WO2016/082088
PCT Pub. Date: Jun. 2, 2016

(65) Prior Publication Data
US 2017/0258364 A1    Sep. 14, 2017

(51) Int. Cl.
*A61B 5/08* (2006.01)
*A61B 5/087* (2006.01)
(Continued)

(52) U.S. Cl.
CPC ............ *A61B 5/087* (2013.01); *A61B 5/0022* (2013.01); *A61B 5/03* (2013.01); *A61B 5/082* (2013.01);
(Continued)

(58) Field of Classification Search
CPC ..... A61B 5/087; A61B 5/0878; A61B 5/0022; A61B 5/746; A61B 5/085; A61B 5/7278;
(Continued)

(56) References Cited

U.S. PATENT DOCUMENTS

| 5,107,860 A | 4/1992 | Malouvier et al. |
| 6,089,548 A * | 7/2000 | Pfitzner .................... B01D 1/00 239/102.2 |

(Continued)

FOREIGN PATENT DOCUMENTS

| CN | 101278838 A | 10/2008 |
| CN | 201453268 U | 5/2010 |

(Continued)

*Primary Examiner* — Navin Natnithithadha
*Assistant Examiner* — Andrey Shostak
(74) *Attorney, Agent, or Firm* — Alan D. Kamrath; Karin L. Williams; Mayer & Williams PC

(57) ABSTRACT

A measurement device for a human respiratory system function comprises a respiration measurement device (20). The respiration measurement device (20) receives a respiratory air flow and senses the respiratory air flow to generate a set of sensing signals, and performs calculation according to the sensing signals to generate a human respiratory system parameter, the sensing signals comprising at least an absolute pressure of the respiratory air flow. The respiration measurement device (20) comprises a respiration measurement channel (21). The absolute pressure generated by a respiratory air flow of a user in the respiration measurement channel (21) that is in a single-end sealed state is measured. The absolute pressure corresponds to the pressure in the lung of the user.

13 Claims, 14 Drawing Sheets

(51) Int. Cl.
*A61B 5/00* (2006.01)
*A61B 5/03* (2006.01)
*A61B 5/085* (2006.01)
*A61B 5/091* (2006.01)
*A61B 5/097* (2006.01)

(52) U.S. Cl.
CPC ............ *A61B 5/085* (2013.01); *A61B 5/0878* (2013.01); *A61B 5/091* (2013.01); *A61B 5/097* (2013.01); *A61B 5/7278* (2013.01); *A61B 5/742* (2013.01); *A61B 5/746* (2013.01)

(58) Field of Classification Search
CPC ........... A61B 5/03; A61B 5/082; A61B 5/097; A61B 5/091; A61B 5/742
See application file for complete search history.

(56) References Cited

U.S. PATENT DOCUMENTS

| | | | |
|---|---|---|---|
| 2010/0286548 A1* | 11/2010 | Lazar | A61B 5/087 600/538 |
| 2011/0021942 A1* | 1/2011 | Choe | A61B 5/097 600/532 |
| 2012/0095304 A1* | 4/2012 | Biondi | G16H 50/20 600/301 |
| 2015/0164340 A1* | 6/2015 | Bedingham | A61B 7/04 600/484 |
| 2016/0106341 A1* | 4/2016 | Adam | A61B 5/087 600/538 |

FOREIGN PATENT DOCUMENTS

| | | |
|---|---|---|
| CN | 103340631 A | 10/2013 |
| CN | 204336917 U | 5/2015 |
| WO | WO2011107684 A1 | 9/2011 |

\* cited by examiner

MEASUREMENT DEVICE AND METHOD FOR HUMAN RESPIRATORY SYSTEM FUNCTION

FIELD OF THE INVENTION

The present invention relates to a human respiratory system function measuring apparatus and method.

BACKGROUND OF THE INVENTION

Air pollution is getting significantly worse in recent years, and the incidence of lung disease is greatly increasing as well. Pulmonary function of a large portion of people has seriously decreased accordingly, and this symptom is not easily to be aware of subjectively. Early stage lung diseases are not easily diagnosed by the patient, and consequently patient's miss the opportunity for early treatment of the disease. A doctor may also neglect potential symptoms if the patient does not inform the doctor. Even if pulmonary radiography is taken, the disease is often discovered after relevant conditions deteriorate. A conventional pulmonary function test is to use a pulmonary function measuring device for testing. A pulmonary function measuring device must be located in a confined space with constant temperature and pressure, and then people must take further steps for pulmonary function tests under the doctor's instruction. However, conventional pulmonary function measuring devices are bulky, the operation is complicated and the test is expensive. Therefore, conventional devices may be neither a household medical equipment, nor portable. These devices are also not operable under exercising conditions. Conventional methods to measure resistances are usually impulse oscillometry and plethysmogrophy, however, the equipment implementing these methods are not only expensive and more complicated while in use, but are also effective only to the patients with moderate conditions; measurement utilizing these methods for patients with mild or severe conditions are less effective. Because these kinds of pulmonary function measuring devices are less convenient, people often miss the opportune time of treatments on early pulmonary lesions due to lack of motivation of regular inspection of pulmonary function. As a result, a cheaper and portable pulmonary function measuring device, which is also capable of wirelessly transmitting the measurement results to the analysis systems in the hospital for informing the users their pulmonary function status, is strongly demanded.

SUMMARY OF THE INVENTION

In order to overcome defects existing in conventional airway resistance measurement devices, a human respiratory system function measuring apparatus is provided and includes a respirometer receiving and sensing a breathing airflow to produce a sensing signal, and producing a human respiratory system parameter by calculating the sensing signal at least includes an absolute pressure of the breathing airflow, wherein, the respirometer includes a respiration measuring pipeline the absolute pressure is generated and measured from the breathing airflow of a user in the respiration measuring pipeline with an end of the respiration measuring pipeline sealed and the absolute pressure corresponds to an intrapulmonary pressure of the user.

The sensing signal further includes a gas flux and a breathing airflow temperature of the breathing airflow sensed in the respiration measuring pipeline, the human respiratory system function measuring apparatus calculates the human respiratory system parameter based on the pressure difference of the breathing airflow, the breathing airflow temperature and the absolute pressure, wherein, a gas density is calculated based on the intrapulmonary pressure and the breathing airflow temperature, a gas flow rate is calculated based on the pressure difference, a gas volume is calculated based on the gas flux, the gas flux is calculated based on the intrapulmonary pressure, the breathing airflow temperature, and the gas flow rate, a vital capacity is calculated based on the gas volume, and a potential energy of the maximum intrapulmonary pressure measured at the time the user starts to exhale after fully inhaled is calculated based on the intrapulmonary pressure and the vital capacity, the potential energy is the product of the intrapulmonary pressure and the vital capacity, a kinetic energy of the exhaled gas converted from the entire potential energy after all gas have been exhaled is calculated based on the gas density and the gas flow rate, the kinetic energy is calculated as: $Qv=\rho \times v2/2$, wherein Qv represents the kinetic energy, $\rho$ represents the gas density, V represents the gas flow rate, an airway resistance indicator representing an airway resistance is calculated based on the potential energy and the kinetic energy, the airway resistance indicator indicates the patency in the respiratory tract while breathing, the airway resistance indicator is calculated by dividing the absolute value of the difference of the potential energy and the kinetic energy by the potential energy: $|Vs-Qv|/Vs$, wherein Vs represents the potential energy and Qv represents the kinetic energy and the loss of the kinetic energy is calculated based on the potential energy and the kinetic energy, wherein the equation of the loss is $Qz=Vs-Qv$, and Qz represents the loss of the kinetic energy.

The respirometer calculates the gas flux from the intrapulmonary pressure, the breathing airflow temperature, and a gas flow rate, characterized in that the respirometer measures a pressure difference generated by the breathing airflow, and calculates the gas flow rate from the pressure difference.

The respirometer includes a measurement module and a signal processing module connected to the measurement module, wherein the measurement module measures the breathing airflow of a user in the respiration measuring pipeline, and outputs the sensing signal to the signal processing module according to the measured result, the signal processing module calculates the human respiratory system parameter based on the sensing signal, and the signal processing module outputs the human respiratory system parameter to a receiving device connected to a database, the database includes a clinical data, the receiving device runs statistics or analysis on the human respiratory system parameter by utilizing the clinical data.

The human respiratory system function measuring apparatus further includes an additional measuring device including a three-way valve, an air pipeline, a respiratory measurement gas pipeline, a measuring pipeline and a control valve, the three-way valve includes three outlet ports communicating with each other, each of the outlet ports is respectively connected to the air pipeline, the a respiratory measurement gas pipeline, and the measuring pipeline, wherein the three-way valve includes a valve block controlling the communication manner among the air pipeline, the respiratory measurement gas pipeline, and the measuring pipeline, and the air pipeline and the respiratory measurement gas pipeline are connected with the control valve, the air pipeline and the respiratory measurement gas pipeline communicate with the outer environment or not depends on the open or closed state of the control valve.

The human respiratory system function measuring apparatus, characterized in that the receiving device outputs a control signal to the signal processing module, and the signal processing module controls the position of the valve block or the open or closed state of the control valve.

The human respiratory system function measuring apparatus may be characterized in that the receiving device utilizes normal human respiratory system parameter from the clinical data as a default threshold, and outputs a warning signal while the human respiratory system parameter exceeds the threshold.

The human respiratory system function measuring apparatus may be characterized in that the respiratory measurement gas pipeline is connected with a steel cylinder, and the respiratory measurement gas pipeline includes a gas analyzing module, wherein by connecting the control valve and the steel cylinder, the control valve controls a respiratory measurement gas inside the steel cylinder to be outputted to the respiratory measurement gas pipeline, and the gas analyzing module analyzes the gas density and the composition of the respiratory measurement gas in the respiratory measurement gas pipeline.

The human respiratory system function measuring apparatus may be characterized in that the respiratory measurement gas pipeline is connected with an air bag, while the control valve is in the opened state, the steel cylinder, the respiratory measurement gas pipeline, and the air bag communicates with each other.

The human respiratory system function measuring apparatus may further include a respiratory mask connected to the respirometer, the respiratory mask including a mask and a connecting port, the profile of the mask corresponds to the shape of the mouth and the nose on a human face, the connecting port is penetrated through the mask, and the respirometer is connected to the respiratory mask through the connecting port.

The human respiratory system function measuring apparatus may be characterized in that the respiratory mask includes a filter membrane and a membrane tightening ring, the appearance of the filter membrane corresponds to a cross-section of the concave surface of the mask the membrane tightening ring is detachably assembled with the mask, the filter membrane is fixed between the membrane tightening ring and the mask.

The human respiratory system function measuring apparatus may be characterized in that the respirometer includes a flow-controlling device, a pressure difference and breathing airflow temperature module measures the pressure difference and the breathing airflow temperature in the respiration measuring pipeline through the flow-controlling device, wherein the flow-controlling device is disposed in the respiration measuring pipeline and includes a constricted section, the inner diameter of the constricted section is smaller than the inner diameter of a free end of the flow-controlling device, so that the pressure difference is formed while gas passes therethrough, the pressure difference and breathing airflow temperature module measures the pressure difference formed in the respiratory measuring pipeline caused by the flow-controlling device.

The human respiratory system function measuring apparatus may further include a nasal respiratory assisting kit assembled with the respirometer, a free end of the nasal respiratory assisting kit having a splitter, and the profile of the splitter corresponding to the width and depth of human nostril.

The human respiratory system function measuring apparatus may further include a cover, wherein the cover is a mouth cover connected with the respirometer or the cover is a nasal cover connected with the nasal respiratory assisting kit, the nasal cover corresponding to the nasal respiratory assisting kit and the width and the depth of human nostril.

According to the foregoing description, the present invention has the following advantages:

1. The structure is simple thus allowing users to carry out self-diagnoses to improve the convenience of lung tests; lung disease patients may be treated earlier by early detection of relevant problems through convenient testing methods.

2. Simplified structure and convenient operations reduces the cost of testing.

3. The signal module can transmit or store the measured data in a specified location in real time to facilitate the tests in subsequent analyses, and the signal of the sensed results can be transmitted wirelessly, for instance: through a wireless network, Bluetooth, infrared, etc. to provide medical personnel convenience on remote monitoring.

4. The invention breaks through conventional methods of measuring resistances, effectively simplifies the measurement equipments, and can also be applied to patients with either mild or severe diseases.

5. The medical staff can remotely control the testing process through the receiving device.

6. By using absolute pressure as a basis on calculating human respiratory system parameters, errors caused by different altitudes of the test sites are greatly reduced.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

Figure 1:
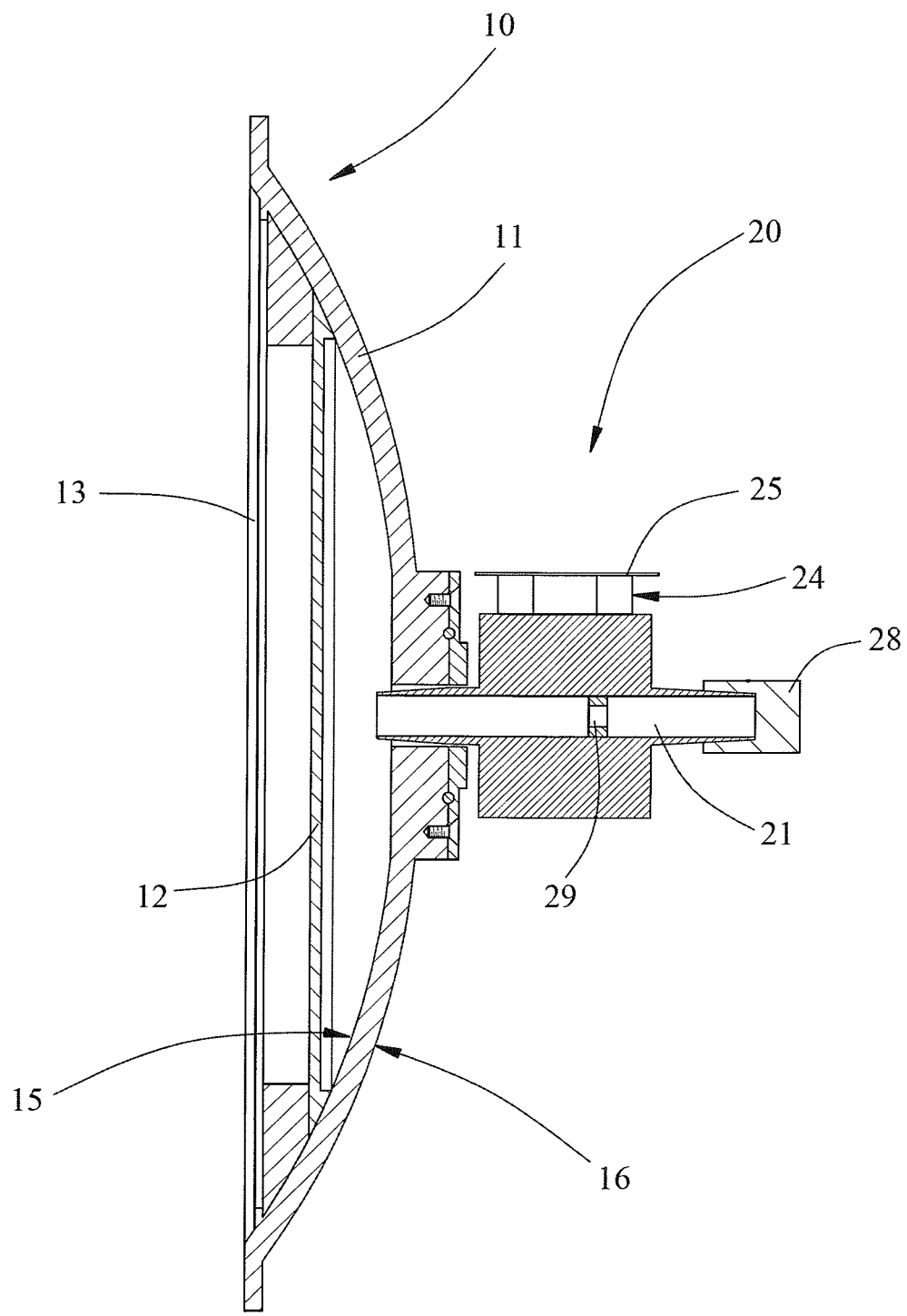
FIG. 1 is a sectional schematic diagram illustrating a human respiratory system function measuring device according to an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts. It is not intended to limit the method or the system by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details. As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that when an element is referred to as being "connected" to another element, it can be directly connected to the other element or intervening elements may be present.

Figure 2:
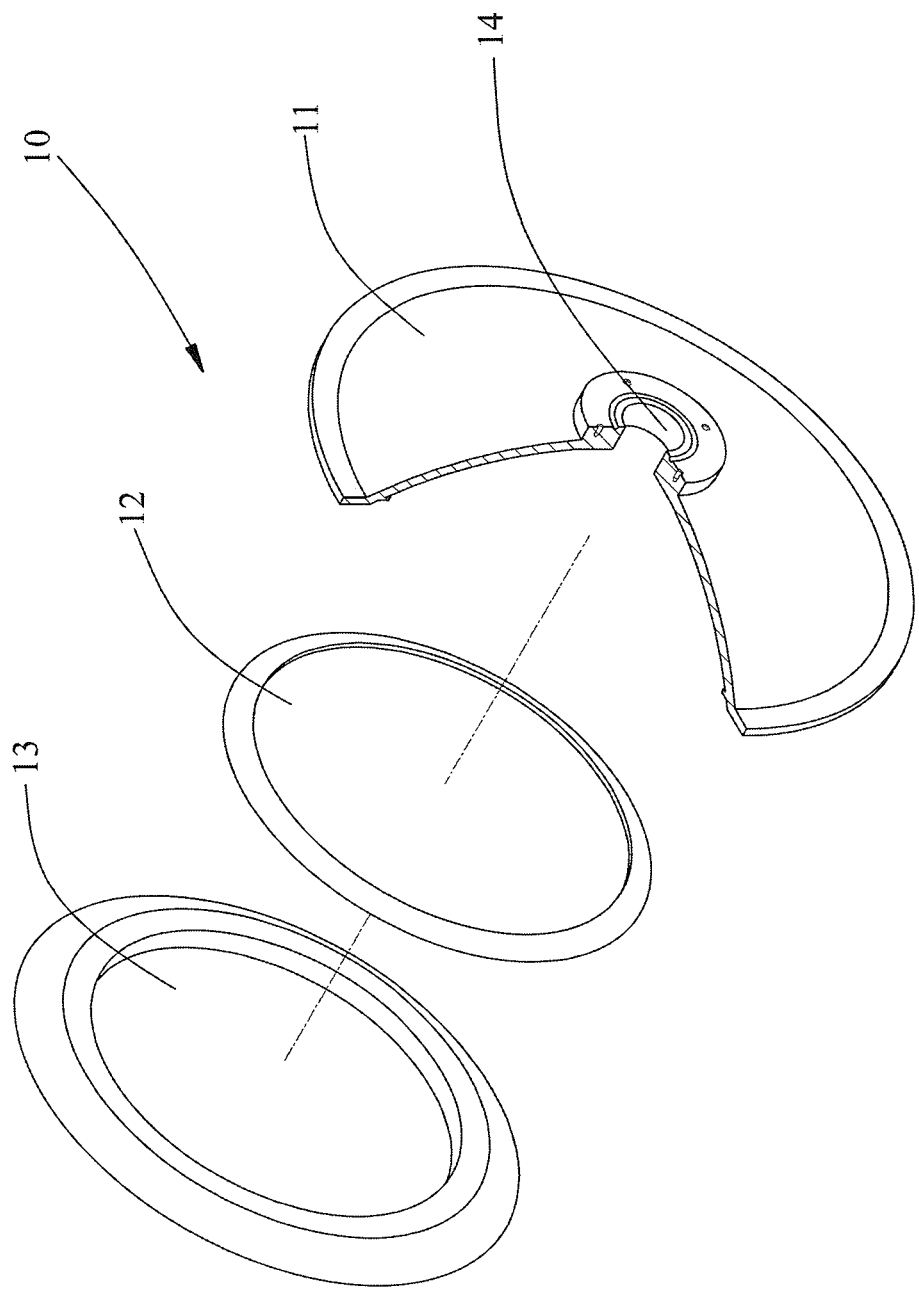
FIG. 2 is an exploded diagram of the respiratory mask according to an embodiment of the present invention.

Referring to FIG. 1 and FIG. 2, a human respiratory system function measuring device is provided and includes a respiratory mask 10 and a respirometer 20. The respiratory mask 10 includes a mask 11 and a connecting port 14, the shape of the mask 11 may be variable. The shape can be a concave surface corresponding to the shape of the nose and the mouth on a human face, or can be a simple rounded concave surface. The mask 11 includes a concave surface 15 and a convex surface 16, the connecting port 14 is penetrated through the mask 11, and the respirometer 20 is connected to the respiratory mask 10 through the connecting port 14. The connection of the respirometer 20 is to be inserted through the connecting port 14 from a direction toward the convex surface 16.

While practicing the present invention to obtain a human respiratory system parameter, the concave surface 15 will be held close to the mouth of the user. A breathing space defined in the concave surface 15 covers the mouth, the user breathes through the respirometer 20, a breathing airflow generated from breathing flows through the respirometer 20, and the respirometer 20 measures and obtains relevant signals from the breathing airflow. The signal will then be processed and calculated via a signal processing module 25 to obtain the human respiratory system parameter, those data including the human respiratory system parameter can be displayed on a receiving device 30. The human respiratory system parameter may include vital capacity (VC), forced vital capacity (FVC), functional residual capacity (FRC), diffusing capacity of the lung for carbon monoxide (DLCO), airway resistance, total lung capacity (TLC), and other relevant data.

The respiratory cover 10 further includes a filter membrane 12 and a membrane tightening ring 13, the appearance of the filter membrane 12 corresponds to a cross-section of the concave surface 15 of the mask 11, the area of the filter membrane 12 is equal or smaller than the cross-section area of the concave surface 15, so that the filter membrane 12 can be detachably and correspondingly assembled with the concave surface 15. The membrane tightening ring 13 is detachably assembled with the mask 11, the filter membrane 12 is fixed between the membrane tightening ring 13 and the mask 11. The filter membrane 12 includes a thin membrane that is capable of filtering air, or may be used to avoid the measurement error caused by reflux of body liquid between the mouth and the nose. The material of the filter membrane 12 can be non-woven fabrics, activated carbon, specific density fabrics and other materials with the effect of filtering air.

Figure 3:
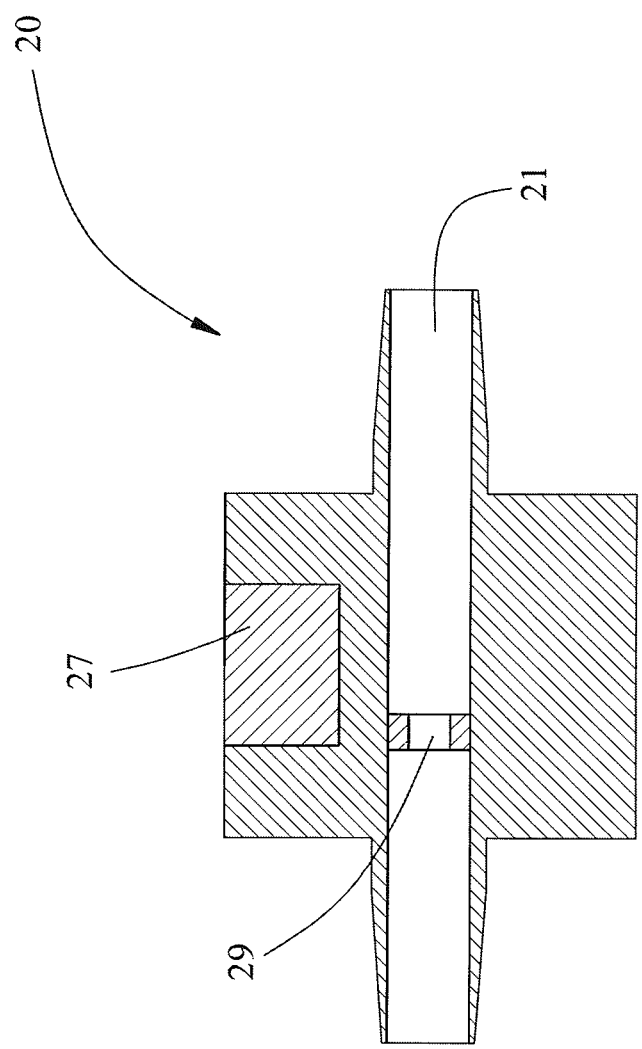
FIG. 3 is a cross-sectional diagram of a respiratory measuring pipeline according to an embodiment of the present invention.
Figure 4:
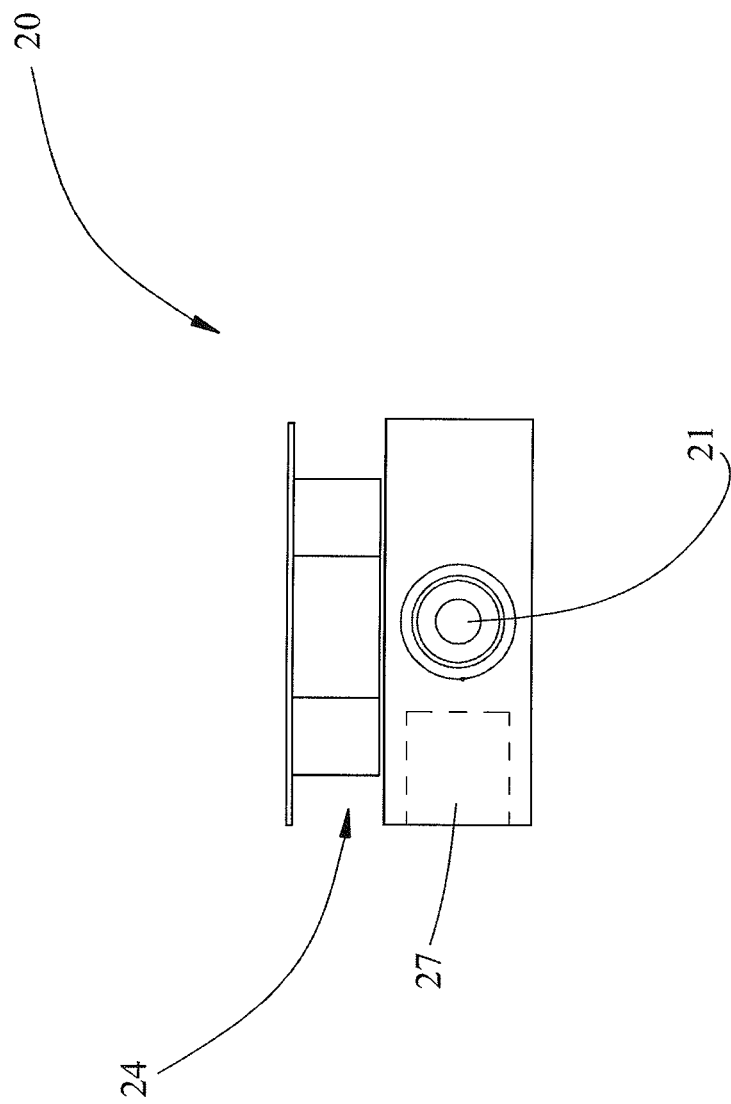
FIG. 4 is a lateral view of a respirometer according to an embodiment of the present invention.

Referring to FIG. 3 and FIG. 4, the respirometer 20 includes a respiration measuring pipeline 21, a measurement module 24, the signal processing module 25, an end seal 28 and a flow-controlling device 29. In which the respiratory measuring pipeline 21 is a hollow pipeline, the breathing airflow from the user may flow through this hollow pipeline. A free end of the respiratory measuring pipeline 21 corresponds to the connecting port 14, the respiratory measuring pipeline 21 can be detachably and tightly assembled with the respiratory mask 10. The connecting manner of the free end and the respiratory mask 10 is not limited to the embodiments depicted herein which may includes tight fit, screw lock, snap, socket, and so on.

Figure 8:
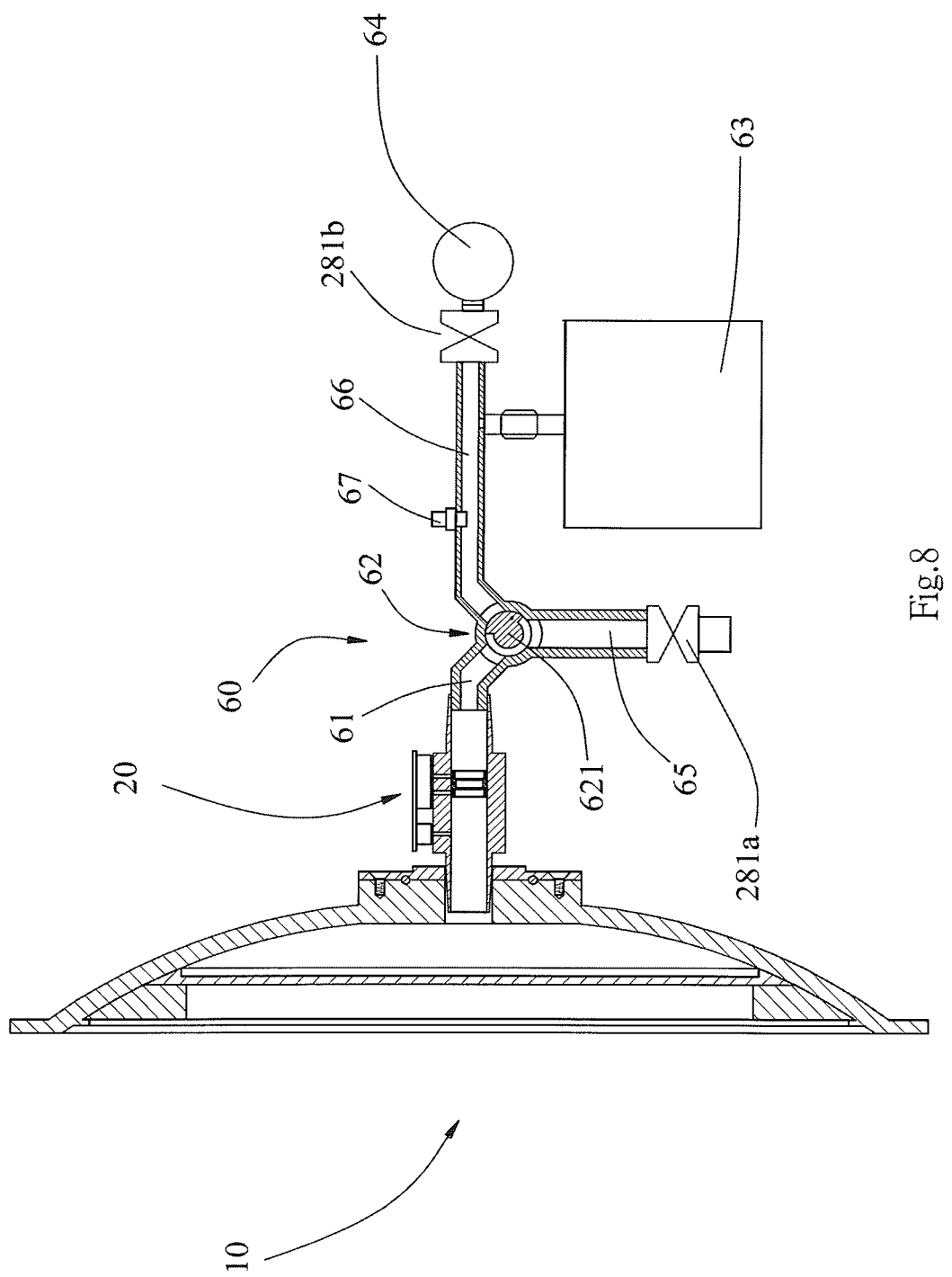
FIG. 8 is a cross-sectional diagram of an additional measuring device according to an embodiment of the present invention.

The end seal 28 is detachably assembled to the other free end of the respiratory measuring pipeline 21, so that the end of the respiratory measuring pipeline 21 can be sealed; alternatively, the end seal 28 can be replaced with a control valve 281. For instance, referring to the control valve 281a shown in FIG. 8, by controlling the state of the control valve 281a to be opened or closed, the respiratory measuring pipeline 21 can be sealed or unsealed accordingly. In an instance that the end seal 28 seals the free end of the respiratory measuring pipeline 21, and the user exhales into the respiratory measuring pipeline 21 through the respiratory mask 10, because the free end of the respiratory measuring pipeline 21 is in a sealed state, the air pressure in the respiratory measuring pipeline 21 equals the air pressure in the lung of the user, a intrapulmonary pressure can be measured and obtained.

Figure 5:
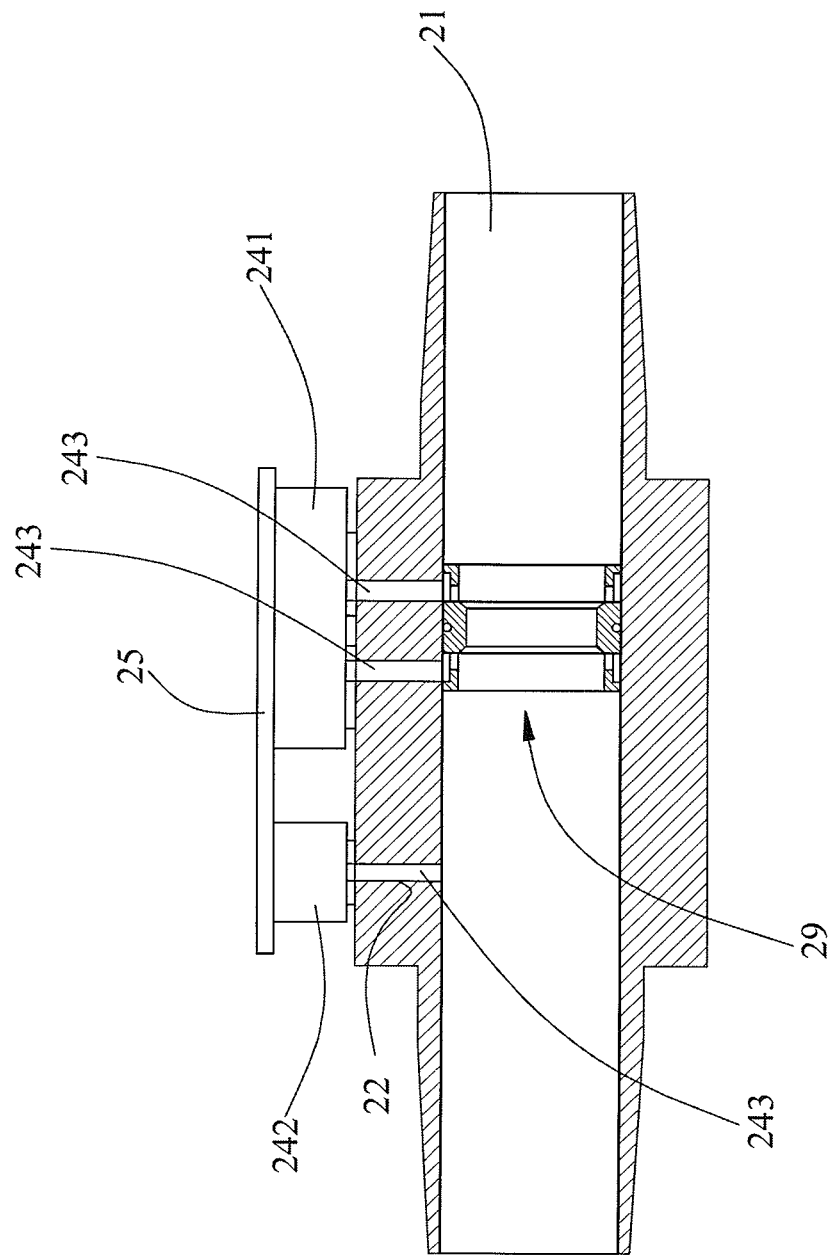
FIG. 5 is a cross-sectional diagram of the respirometer according to an embodiment of the present invention.
Figure 6:
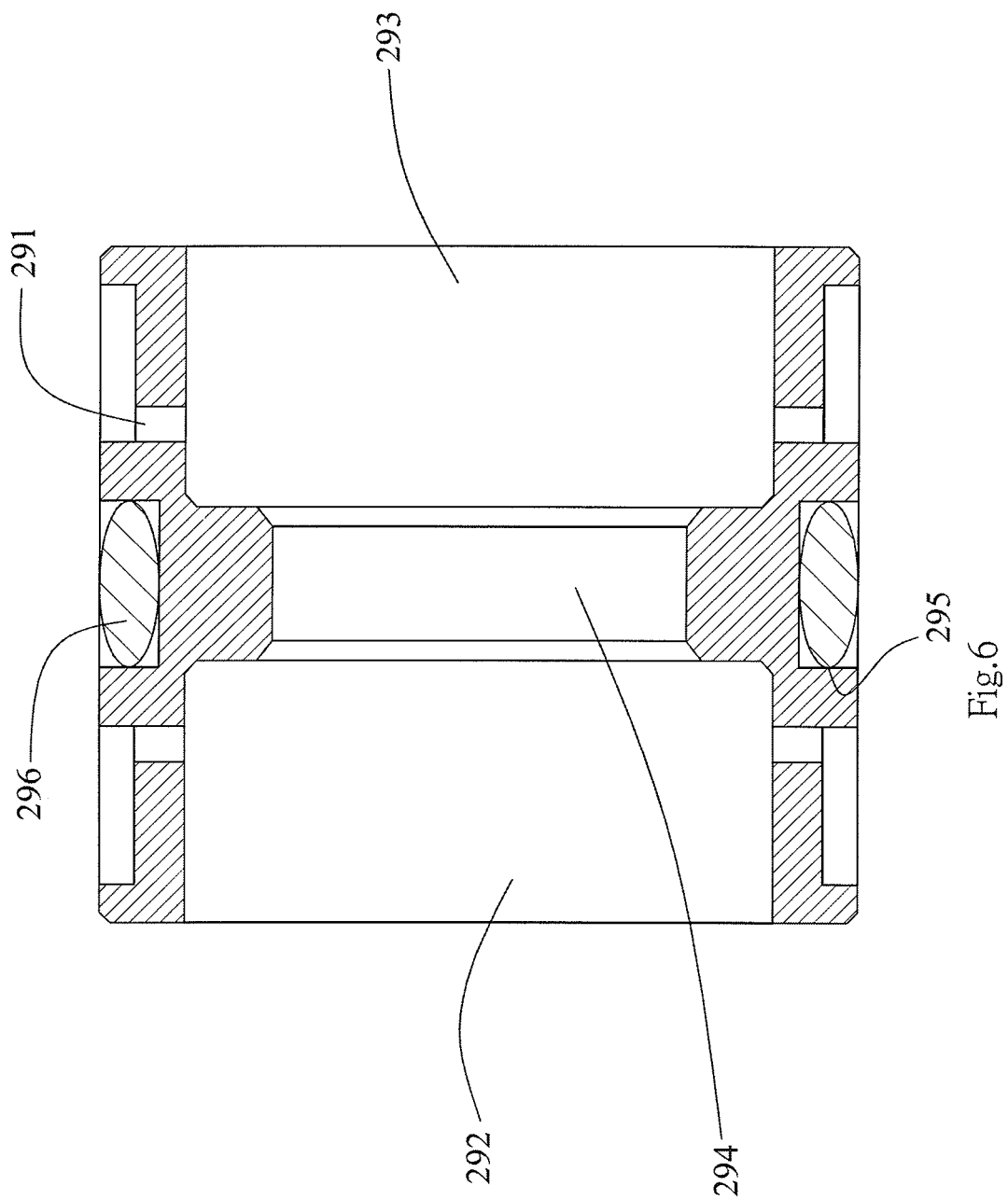
FIG. 6 is a cross-sectional diagram of a flow-controlling device according to an embodiment of the present invention.

Referring to FIG. 5 and FIG. 6, the flow-controlling device 29 is disposed in the respiratory measuring pipeline 21, the flow-controlling device 29 is a ring-like structure, such that the breathing airflow from the user may flow through the flow-controlling device 29 via its two free ends. A pressure difference generated by the breathing airflow of the user while flowing through the flow-controlling device 29 in the respiratory measuring pipeline 21 can be measured by the measurement module 24. The flow-controlling device 29 includes at least a pressure guiding port 291, an inlet port 292, an outlet port 293, a constricted section 294, and a sealing ring receiving recess 295. The inlet port 292 and the outlet port 293 are the two free ends of the flow-controlling device 29, the constricted section 294 is formed in the middle of the flow-controlling device 29, in which the inner diameter of the constricted section 294 is smaller the inner diameters of both the inlet port 292 and the outlet port 293, so that a change of airflow rate is occurred according to the resistance due to different inner diameters while the airflow passing through the flow-controlling device 29, thereby generating the pressure difference between the inlet port 292 and the outlet port 293. The pressure guiding port 291 is formed on the outer periphery of the flow-controlling device 29, in which the pressure guiding port 291 penetrates through the flow-controlling device 29 so as to communicate the flow-controlling device 29 with the outer environment through the pressure guiding port 291. According to an embodiment of the present invention, a number of the pressure guiding ports 291 are formed at the outer periphery of the inlet port 292 and the outlet port 293 and arranged symmetrically about the constricted section 294. The distances from each pressure guiding port 291 of the two free ends to the center, namely the constricted section 294, are equal. As a result, the pressure formed inside the flow-controlling device 29 can be precisely measured by the measurement module 24. The sealing ring receiving recess 294 may contain a sealing ring 296, so that the airflow can completely pass through the flow-controlling device 29 by avoiding leakage between the flow-controlling device 29 and the inner wall of the respiratory measuring pipeline 21, which causes measurement errors.

The measurement module 24 includes a pressure difference and breathing airflow temperature module 241 and a pressure module 242, the measurement module 24 disposed adjacent to the respiratory measuring pipeline 21. For instance, the measurement module 24 may be disposed at the outer periphery of the respiratory measuring pipeline 21, or to be disposed inside the respiratory measuring pipeline 21. According to an embodiment of the present invention, variations of the pressure, the gas flux, and the breathing airflow temperature inside the respiratory measuring pipeline 21 can be measured by the measurement module 24 with a sensing end 243 that penetrates through at least one sensing port 22. A sensing signal will be outputted to the signal processing module 25 after the sensing end 243 senses the variations of those physical quantities mentioned above. The sensing port 22 is formed at the outer periphery of the respiratory measuring pipeline 21 and penetrates through the respirometer 20, so as to communicate the respiratory measuring pipeline 21 to the outer environment through the sensing port 22.

The pressure module 242 has the sensing end 243, wherein the pressure inside the respiratory measuring pipeline 21 may be measured via the sensing end 243, during such measurement, one of the free ends of the respiratory measuring pipeline 21 is sealed by the end seal 28 or other applicable sealing manners, and the sensing signal of variations of physical quantities including the air pressure is outputted from the measurement module 24 to the signal processing module 25.

The air pressure measured by the pressure module 242 is presented as an absolute pressure, thus avoiding measurement errors while the measurement of the pressure module 242 is taken in different latitudes, which causes the measured intrapulmonary pressure of the user to not be obtained correctly. According to an embodiment of the present invention, after measuring a relative pressure inside the respiratory measuring pipeline 21 by the pressure module 242, the altitude of the location where the measurement has been taken will be further considered and used to obtain a relative atmospheric pressure, and by adding the relative pressure to the relative atmospheric pressure of where the measurement has been taken, the absolute pressure is obtained. The altitude information of the measurement site can be received externally, such as being received by a GPS (Global Positioning System) device capable of obtaining the altitude of the measurement site, and the relevant atmospheric pressure of such altitude. Alternatively, the altitude information may also be manually inputted by the user via an input device connected to the measurement module 24.

Conventionally, relative pressure is often presented as the result in pressure measurements, in which the atmospheric pressure is set as a zero reference point, where the pressure value lower than the atmospheric pressure is defined as a negative value, and defined as a positive value in an opposite condition. However, the atmospheric pressure varies upon the altitude, by referring to basic knowledge:

"atmospheric pressure decreases as the altitude increases, the relationship in which is that for each 12-meter increment of the altitude, the atmospheric pressure decreases for 1 mm-Hg, or, for each 9-meter increment of the altitude, the atmospheric pressure decreases for 100 pa."

Based on the aforementioned knowledge, the conventional pressure measurements of presenting the results in relative manners easily causes measurement errors due to latitude variations of the measurement site. Pressures measured by the present invention are presented in absolute values instead of relative values, so that measurement errors are unlikely to appear.

Figure 7:
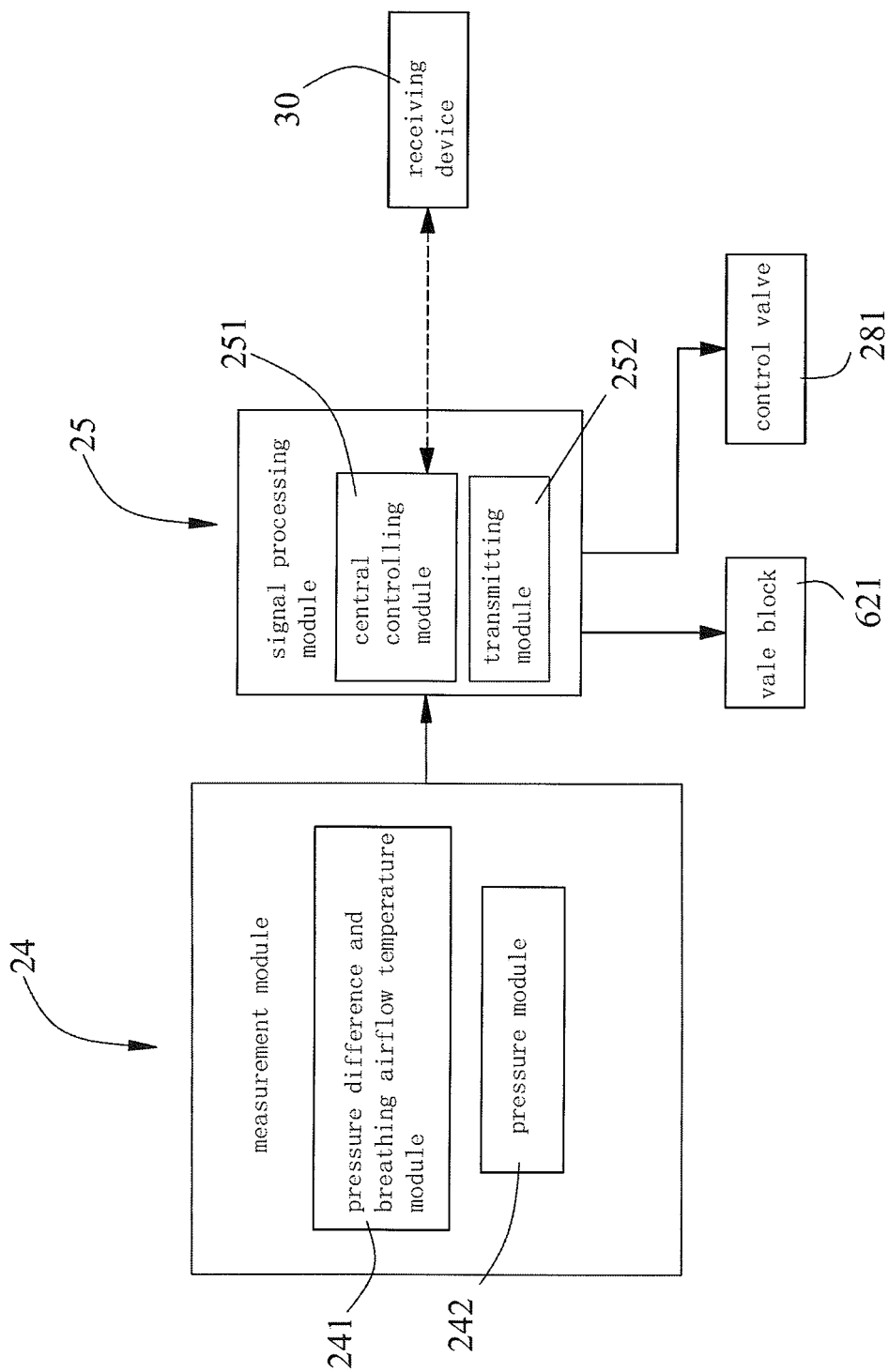
FIG. 7 is a functional block diagram according to an embodiment of the present invention.

In regard with the gas flux and breathing airflow temperature module 241, the measurement of gas flux can be performed in an ultrasonic or heat conducting manners. According to an embodiment of the present invention, measurement of the gas flux of the pressure difference and breathing airflow temperature module 241 is performed by utilizing a differential pressure sensing manner to measure the pressure difference in the respiratory measuring pipeline 21. Then, the gas flux can be calculated from the pressure difference, in which the embodiment includes at least two of the sensing ends 243 respectively inserted into two of the sensing ports 22, the two sensing ports 22 respectively correspond to the two pressure guiding ports 291 of the flow-controlling device 29, the two pressure guiding ports 291 respectively formed at two ends of the constricted section 294, so as to measure the pressure difference of the two ends of the flow-controlling device 29 and the breathing airflow temperature by the pressure difference and breathing airflow temperature module 241. Further, the two pressure guiding ports 291 are arranged in a symmetrical manner about the constricted section 294 and disposed at the inlet port 292 and the outlet port 293, so that the pressure difference of the two ends of the flow-controlling device 29 and the breathing airflow temperature can be measured more precisely by the pressure difference and breathing airflow temperature module 241. The sensing signal which includes the variation of physical quantities of the pressure difference and the breathing airflow temperature is outputted from the measurement module 24 to the signal processing module 25. Referring to FIG. 7, the signal processing module 25 can be connected to the measurement module 24 by wire or wirelessly. When connected by wire, the signal processing module 25 can directly receive the sensing signal outputted from the measurement module 24, or, when connected wirelessly, the measurement module 24 may wirelessly transmit the sensing signal to the signal processing module 25, so that the signal processing module 25 can be wirelessly connected to the measurement module 24, in which the wireless connection can be performed by various manners such as WLAN, Bluetooth, infrared, and so on.

According to an embodiment of the present invention, the measurement of the gas flux is performed in the ultrasonic manner, and two ultrasonic sensing devices are further provided and disposed at the outer periphery of the respiratory measuring pipeline 21 in an interval arrangement. The gas flux is calculated by using an ultrasonic wave produced from the ultrasonic sensing device, and the reflecting time period of the ultrasonic wave. When the measurement of the gas flux is performed in the heat conducting manner, a heating device is further provided at the inlet port 292 in the respiratory measuring pipeline 21, in which the gas flux is calculated based on the increment of the airflow temperature in the respiratory measuring pipeline 21.

The signal processing module 25 includes a central controlling module 251 and a transmitting module 252. After the transmitting module 252 receives the sensing signal outputted from the measurement module 24, the central controlling module 251 performs analyses and calculations on the sensing signal, the transmitting module 252 then outputs the human respiratory system parameter based on the result of the analyses and calculations to the receiving device 30, in which the receiving device 30 may be a mobile communication device, a mobile phone, a personal computer, a tablet computer, or a website page displaying the human respiratory system parameter via a network server. The transmission between the transmitting module 252 and the receiving device 30 can be done by wire or wirelessly, for instance, the signal processing module 25 can be connected to the receiving device 30 via a wired network, or can be connected to the receiving device 30 wirelessly via WLAN, Bluetooth, infrared, etc., for transmitting the human respiratory system parameter to the receiving device 30, and further data storing, analyses, statistical estimations via the receiving device 30, or issuing a warning signal according to the human respiratory system parameter to the receiving device 30. Furthermore, the receiving device 30 can be connected to a database, in which the database may include clinical data like normal or abnormal human respiratory system parameter data, relationships of the changes in the atmospheric pressure by different altitudes, or a normal range of vital capacities, or other data obtained from healthy human bodies via measurement on the human respiratory system parameter. The receiving device 30 utilizes the clinical data to run statistics or analyze the human respiratory system parameter, for instance, the receiving device 30 utilizes normal human respiratory system parameter from the clinical data as a default threshold, and issues a warning signal while the human respiratory system parameter exceeds the threshold.

A power supply module 27 can be fixed or detachably disposed on the respirometer 20 for supplying electrical power needed to the measurement module 24 or the signal processing module 25, in which the power supply module 27 may be an adapter connected to an electrical socket, or a replaceable battery.

Figure 9:
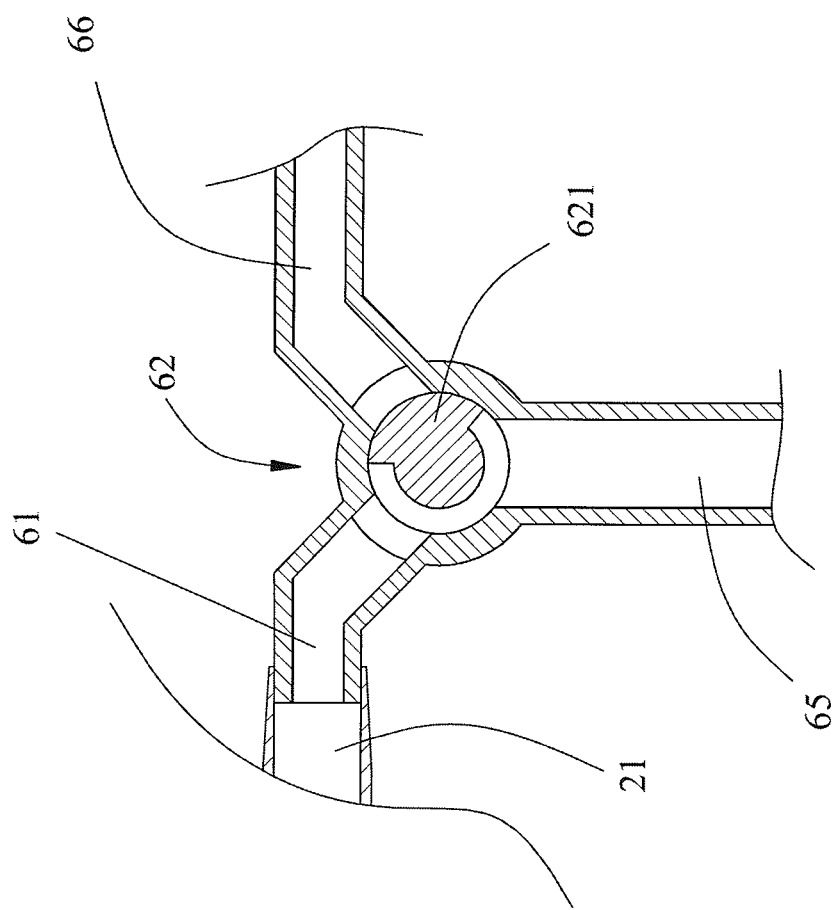
FIG. 9 is a cross-sectional diagram of a three-way valve in a first position according to an embodiment of the present invention.
Figure 10:
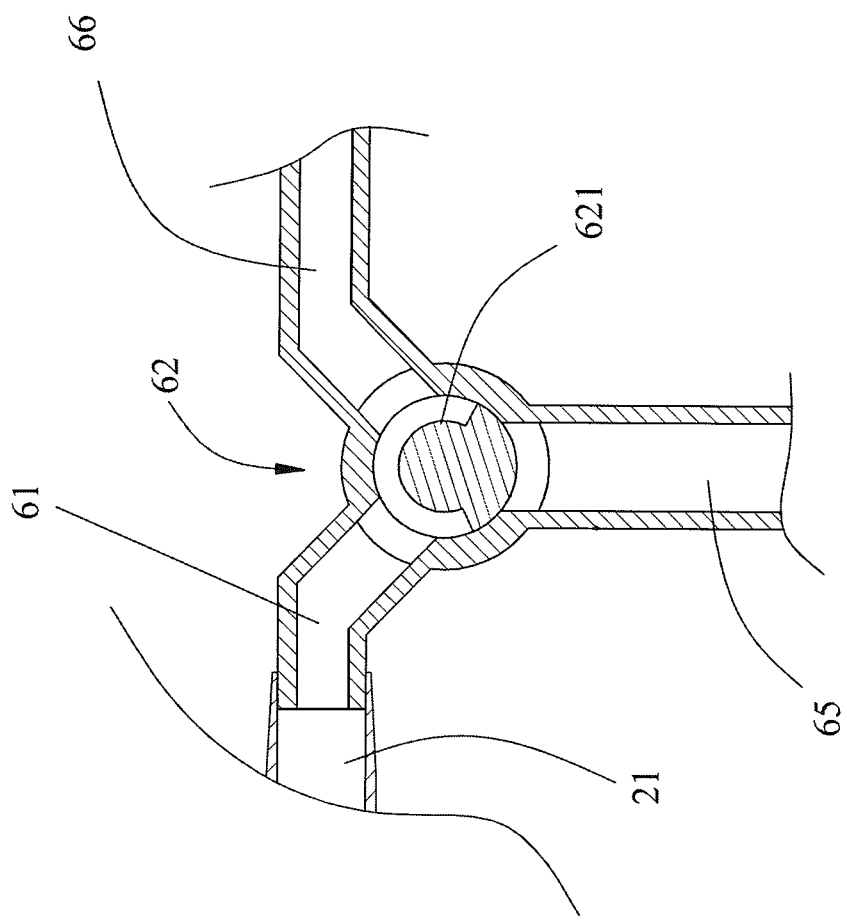
FIG. 10 is a cross-sectional diagram of the three-way valve in a second position according to an embodiment of the present invention.

Referring to FIG. 9 and FIG. 10, the respirometer 20 is connected to an additional measuring device 60, by utilizing the additional measuring device 60, tests of vital capacity, residual capacity or diffusing capacity can be performed, the sensing signal may be outputted from the respirometer 20 to the signal processing module 25 according to the result of the tests, and then the signal processing module 25 outputs the human respiratory system parameter to the receiving device 30 after calculation. Additionally, the respirometer 20 can be connected to the respiratory mask 10 or a nasal respiratory assisting kit 40. The additional measuring device 60 includes a three-way valve 62, a steel cylinder 64, an air bag 63, an air pipeline 65, a respiratory measurement gas pipeline 66, a measuring pipeline 61, a number of control valves 281a and 281b, and a gas analyzing module 67, in which the three-way valve 62 has three outlet ports communicating with each other, each of the outlet ports respectively is connected to the measuring pipeline 61, the respiratory measurement gas pipeline 66, and the air pipeline 65.

The gas analyzing module 67 is disposed on the respiratory measurement gas pipeline 66, the gas analyzing module 67 measures the gas density or composition inside the respiratory measurement gas pipeline 66 via a probe. The respiratory measurement gas pipeline 66 is connected with the air bag 63, thereby communicating the respiratory measurement gas pipeline 66 with the air bag 63, and a gas for respiratory measurement use released from the steel cylinder 64 can be stored in the air bag 63. The air bag 63 is made of elastic materials (ex. rubber, silicon or other high polymer materials or leather), so that the air bag 63 may expand upon increment of the gas volume contained in order to increase its storage capacity. A free end of the respiratory measurement gas pipeline 66 opposing to an outlet port of the three-way valve 62 is connected to the steel cylinder 64, the steel cylinder 64 contains the gas for respiratory measurement use, which can be used to perform various lung function tests, in which the control valve 281b controls the steel cylinder 64 to be opened or closed, and when the control valve 281b is opened, the gas for respiratory measurement use will be released from the steel cylinder 64, the gas for respiratory measurement use may be 0.3% by weight of carbon monoxide (CO), or helium, or oxygen or other special gas. The term "diffusion" represents the gas exchange process of oxygen and carbon dioxide between alveolar and capillaries via alveolar capillary membrane. Diffusion function is indicated by diffusion capacity, which indicates the gas amount passed per minute when the difference of the partial pressures on both sides of the alveolar capillary membrane equals 0.1333 kpa (1 mmHg). Diffusion disorder is mainly in regard with oxygen. The testing method is to use carbon monoxide as the measurement gas, for which the advantages include: 1) except those severe smokers, the amount of carbon monoxide (CO) entering capillary and mixing with venous blood almost equals zero, therefore can be ignored during calculation. 2) Hemoglobin affinity of carbon monoxide (CO) is 210 times higher than the oxygen, during inhalation of a small amount of carbon monoxide (CO) to the plasma through the capillary membrane, the carbon monoxide rapidly accesses red blood cells and binds with hemoglobin, and that the partial pressure of carbon monoxide (CO) in the plasma equals zero, and is ignorable as well during subsequent calculations.

While the air pipeline 65 communicates with the respiratory measurement gas pipeline 66, the gas for respiratory measurement test in the respiratory measurement gas pipeline 66 can be exhausted through the air pipeline 65, in which the air pipeline 65 is connected with the control valve 281a, the gas for respiratory measurement test can be exhausted through the air pipeline 65 while the control valve 281a is opened. The free end of the respiratory measurement gas pipeline 66 is opposite to the outlet port of the three-way valve 62.

The measuring pipeline 61 is connected to the respirometer 20, so that the user may breath through the respirometer 20 in order to undergo various lung function tests (ex. vital capacity test, residual capacity test, or diffusing capacity test), in which the control valve 281 is connected in between the air pipeline 65 and the respirometer 20, the breathing airflow from the user may be flown into the additional measuring device 60 while the control valve 281 is opened.

The position change of a valve block 621 in the three-way valve 62 relates to the communication state of the three-way valve 62, the valve block 621 can be sealed at one of the outlet ports of the three-way valve 62 in order to communicate the two other outlet ports. While positioning the valve block 621 is a first position in the three-way valve 62, the measuring pipeline 61 communicates with the air pipeline 65, by connecting the respirometer 20 and the measuring pipeline 61, the user may breath through the respirometer 20 in order to determine the vital capacity (VC) or the total lung capacity (TLC) of the user, during calculation, and while the valve block 621 is positioned at the first position, the control valve 281a is in a opened state, and that the breathing airflow from the user can be entering the respirometer 20 through the additional measuring device 60, and to obtain the vital capacity or the total lung capacity through calculation of the pressure module 242 and the pressure difference and breathing airflow temperature module 241. By controlling the state of the control valve 281a into a closed state, a confined space is defined by the air pipeline 65, the measuring pipeline 61, and the hollow pipeline of the respirometer 20, when the user exhales into the additional measuring device 60 through the respirometer 20, the air pressure inside the confined space increases, and that the air pressure inside the confined space can be measured by the pressure module 242 in order to obtain the intrapulmonary pressure.

After positioning the valve block 621 in the first position in the three-way valve 62, the respiratory measurement gas pipeline 66 is sealed due to the position of the valve block 621, and the control valve 281b which controls the steel cylinder 64 is opened, the respiratory measurement gas pipeline 66 and the air bag 63 will then be filled with the gas for respiratory measurement use, which is needed for quantitative tests. The gas analyzing module 67 will then be calibrated, and the gas analyzing module 67 measures the gas density and composition inside the respiratory measurement gas pipeline 66, so that the residual volume (RV), the functional residual capacity (FRC), and the diffusing capacity of the lung for carbon monoxide (DLCO) of the user may be tested. According to an embodiment of the present invention, a gas standard is determined as 0.3% by weight of carbon monoxide, and the concentration value measured by the gas analyzing module 67 should be same as the gas standard, i.e., 0.3% by weight of the carbon monoxide content, and if any deviation exist, a recalibration can be performed.

Figure 11:
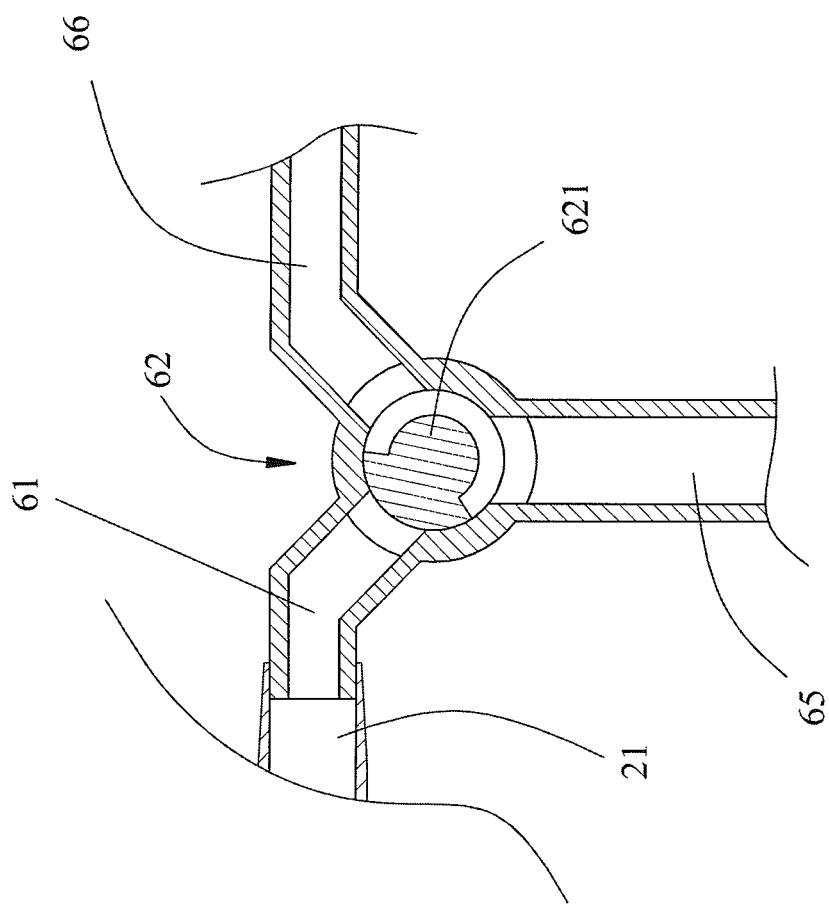
FIG. 11 is a cross-sectional diagram of the three-way valve in a third position according to an embodiment of the present invention.

When the valve block 621 is positioned in a second position in the three-way valve 62, the respiratory measurement gas pipeline 66 communicates with the measuring pipeline 61, so that the gas analyzing module 67 may measure the gas density and the composition inside the respiratory measurement gas pipeline 66. As a result, the residual volume (RV) of the user may be obtained by inhaling the gas for respiratory measurement use. The gas analyzing module 67 may conduct gas concentration and composition analyses by using physical and chemical properties, such as using semiconductor type (surface controlled type, volume controlled type, surface potential type), catalytic combustion type, solid thermal conductivity type or the like, or by using physical properties conducting gas concentration and composition analyses: such as thermal conductivity, optical interference, infrared absorption, etc., or by using electrochemical properties conducting gas concentration and composition analyses: such as using constant potential electrolysis, Galvanic cell, membrane type ion-selective electrode, fixed electrolyte type and so on. As shown in FIG. 11, when the valve block 621 is changed to a third position in the three-way valve 62, the respiratory measurement gas pipeline 66 communicates with the air pipeline 65 to open the control valve 281a so that the air bag 63 exhausts the contained gas for respiratory measurement use to be reused next time.

All of the foregoing sensing signals from the measuring module 24 and the additional measuring device 60 will be transmitted to the signal processing module 25, the signal processing module 25 calculates and outputs the human respiratory system parameter to the receiving device 30, in which the sensing signal includes:

1. Intrapulmonary pressure (P): the pressure module 242 measures the internal air pressure of the respiratory measuring pipeline 21 having one of the free end sealed with the end seal 28, or the internal air pressure of the respiratory measuring pipeline 21 after assembling with the additional measuring device 60 and positioning the valve block 621 to be in the first position in the three-way valve 62 with the control valve 281a in a closed state, these internal air pressures equal the intrapulmonary pressure (P) of the user;

2. Pressure difference ($\Delta P$): which is the pressure difference ($\Delta P$) generated inside the respiratory measuring pipeline 21 while the user breathes and measured by the pressure difference and breathing airflow temperature module 241;

3. Breathing airflow temperature (T): which is the breathing airflow temperature (T) inside the respiratory measuring pipeline 21 while the user breathes and measured by the pressure difference and breathing airflow temperature module 241;

4. Gas density: which is the gas density in the respiratory measurement gas pipeline 66 analyzed by the gas analyzing module 67.

The human respiratory system parameter includes the following data:

1. Gas density ($\rho$): the gas density ($\rho$) is calculated by the central controlling module 251 from the intrapulmonary pressure (P) and the breathing airflow temperature (T);

2. Gas flow rate (V): the gas flow rate (V) is calculated by the central controlling module 251 from the pressure difference ($\Delta P$);

3. Gas volume (L): the gas volume (L) equals the vital capacity or the total lung capacity that corresponds to the gas flux (Q) in the breathing measurement pipe 21 measured by the breathing measurement device 20;

4. Gas flux (Q): the gas flux (Q) is calculated by the intrapulmonary pressure (P), the breathing airflow temperature (T), and the gas flow rate (V);

5. Potential energy (Vs): which is the potential energy of the maximum intrapulmonary pressure that can be measured by the respirometer 20 at the time the user starts to exhale after fully inhaled. When the user is fully inhaled, a degree of pressure of the air inside the lung exists and has the potential energy. The potential energy (Vs) is the product of the intrapulmonary pressure (P) and the vital capacity, in which the vital capacity can be obtained from the gas volume (L), the function of the potential energy being the product of the intrapulmonary pressure (P) and the vital capacity is: the potential energy (Vs)=f (intrapulmonary pressure (P)×the vital capacity).

6. Kinetic energy (Qv): which is converted from the entire potential energy after all gas have been exhaled, the kinetic energy can be obtained based on the gas density ($\rho$) and the gas flow rate (V), the relationship can be expressed as: $Qv = \rho \times v^2 / 2$.

7. Airway resistance (R): which is the indicator representing an airway resistance, namely the patency in the respiratory tract while breathing, and is evaluated based on the energy loss in the respiratory tract. Because of existing resistance in the airway of the user, only a part of the potential energy (Vs) is converted into the kinetic energy (Qv), and the loss part reflects the resistance in the airway, which is calculated as (Vs−Qv) representing the parameter of the airway resistance (R).

An airway resistance indicator can be calculated from the potential energy (Vs) and the kinetic energy (Qv), the airway resistance indicator is calculated by dividing the absolute value of the difference of the potential energy (Vs) and the kinetic energy (Qv) (|Vs−Qv|) by the potential energy (Vs); airway resistance indicator (|Vs−Qv|/Vs) is a ratio having significant clinical meanings.

8. Loss of the kinetic energy (Qz): which is the loss of the kinetic energy (Qv) converted from the potential energy (Vs) during exhalation due to the airway resistance (R), and that the relationship of the loss of the kinetic energy (Qz), the potential energy (Vs) and the kinetic energy (Qv) can be expressed as: the potential energy (Vs)=the kinetic energy (Qv)+the loss of the kinetic energy (Qz). Because that the potential energy (Vs) and the kinetic energy (Qv) are known, the loss of the kinetic energy (Qz) can be calculated.

After the measurement of the gas density inside the respiratory measurement gas pipeline 66 by the gas analyzing module 67, the sensing signal is outputted to the signal processing module 25, the central controlling module 251 controls the states of the control valve 281a, 281b, and the three-way valve 62 in the additional measuring device 60 according to the sensing signal. For instance, according to the purpose of the measurement, such as measurements of the vital capacity or the total lung capacity, the central controlling module 251 drives the valve block 621 of the three-way valve 62 to be positioned in the first position. Meanwhile, for measuring performance of respiratory dynamics of the lung, the state of the control valve 281a can be controlled, or, for performing residual capacity, function residual capacity, diffusing capacity tests, the central controlling module 251 controls the control valve 281b to be opened or closed in order to release the gas for respiratory measurement use from the steel cylinder 64.

According to an embodiment of the present invention, the additional measuring device 60 can be controlled by the receiving device 30, the valve block 612 and the control valves 281a, 281b, of the additional measuring device 60 are electrically connected to the signal processing module 25, the receiving device 30 outputs a control signal to the signal processing module 25, and the central controlling module 251 controls the states of the control valves 281a, 281b in the additional measuring device 60 or the valve block 621 in the three-way valve 62, for instance, medical personnel may control the valve block 621 to be positioned in the first, second, or third position through the receiving device 30 according to different test purposes, or, the states of the control valves 281a and 281b.

The gas analyzing module 67 is electrically connected to the signal processing module 25, the gas analyzing module 67 and the measurement module 24 may issue a warning signal to the signal processing module 25 according to the measurement result, the signal processing module 25 then delivers the warning signal to the receiving device 30. According to an embodiment of the present invention, the measurement module 24 and the gas analyzing module 67 has a default warning threshold, the warning threshold can be an upper boundary, a lower boundary, or a predetermined range of a measured value, for example, in a measuring module 24 perspective, the warning threshold may be the lowest gas flux, the lowest gas volume, the highest airway resistance, etc., and in a gas analyzing module 67 perspective, the warning threshold can be the whether the gas density or the composition of the gas for respiratory measurement use is correctly presented. By issuing the warning signal, the remote controlling medical personnel may know the situation instantly via the receiving device 30.

Figure 12:
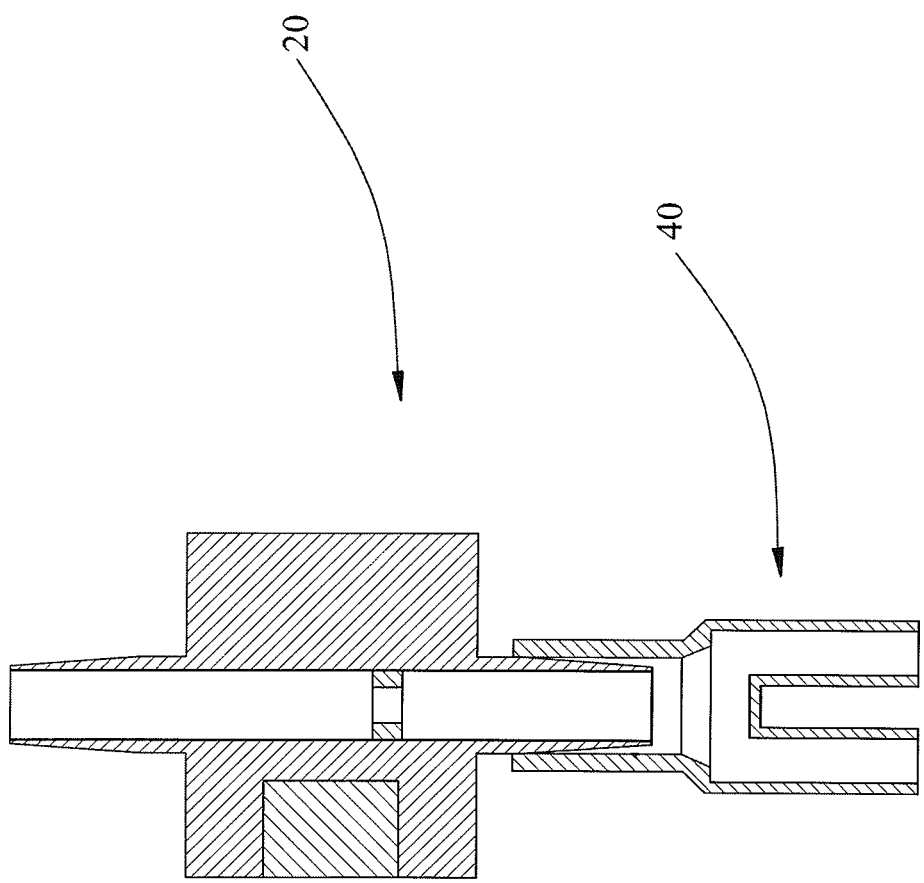
FIG. 12 is a cross-sectional diagram of a nasal respiratory assisting kit according to an embodiment of the present invention.

Referring to FIG. 12, the present invention further includes the nasal respiratory assisting kit 40 adapted to be assembled with the respirometer 20, and providing an alternative option to let the user undergo the tests via nasal respiration, in which a free end of the nasal respiratory assisting kit 40 has a splitter, the profile of the splitter corresponding to the width and depth of human nostril, so as to connect with the human nostril.

According to an embodiment of the present invention, when the respirometer 20 is assembled with the nasal respiratory assisting kit 40, the airway resistance measured includes the resistance of the pulmonary respiratory tract and the resistance of the laryngeal and nasopharynx respiratory tract, so that the airway resistance of the laryngeal and nasopharynx can be calculated by the airway resistance that includes the nasopharynx and pulmonary respiratory tract, minus the airway resistance that only includes the pulmonary respiratory tract. The airway resistance of the laryngeal and nasopharynx can be used as a reference index for determining the degree of smoothness of the patient during sleep, for example, to diagnose a symptom of sleep apnea or snoring.

Figure 13:
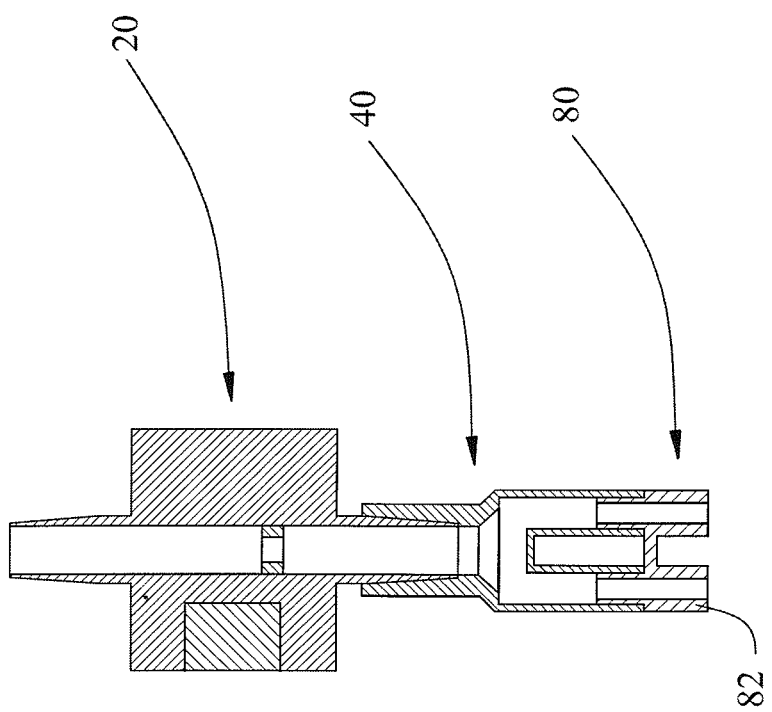
FIG. 13 is a cross-sectional diagram of a cover according to an embodiment of the present invention.
Figure 14:
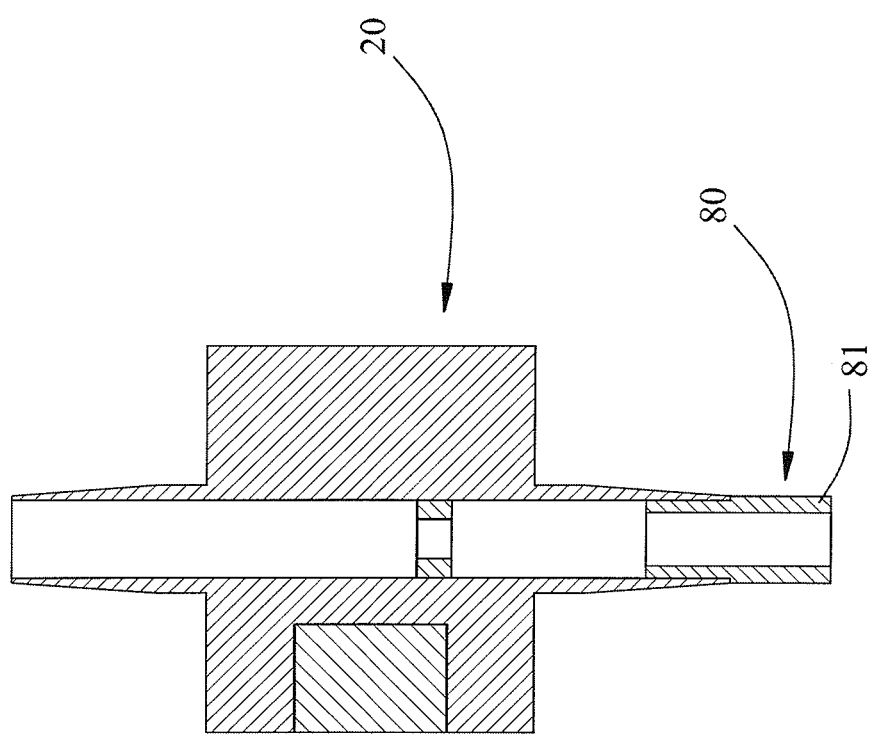
FIG. 14 is a cross-sectional diagram of a nostril cover according to an embodiment of the present invention.

Referring to FIG. 13 and FIG. 14, and according to an embodiment of the present invention, a cover 80 is further included. The cover 80 is adapted to be assembled with the respirometer 20, and can be disposable each time the cover 80 has been used, in order to stay clean during measurements. For instance, the cover 80 is a mouth cover 81 detachably connected with the respirometer 20, the mouth cover 81 can be in a cylinder-like shape or a flat cylinder shape, so as to easily engage the mouth. Alternatively, the cover 80 can be a nasal cover 82 having two splitters at the two respective free ends, in which the two free ends can be correspondent to the nasal respiratory assisting kit 40 and the width and the depth of the human nostril.

According to the foregoing description, the present invention has the following advantages:

1. The structure is simple thus allowing users to carry out self-diagnoses to improve the convenience of lung tests; lung disease patients may be treated earlier by early detection of relevant problems through convenient testing methods.

2. Simplified structure and convenient operations reduces the cost of testing.

3. The signal module can transmit or store the measured data in a specified location in real time to facilitate the tests in subsequent analyses, and the signal of the sensed results can be transmitted wirelessly, for instance: through a wireless network, Bluetooth, infrared, etc. to provide medical personnel convenience on remote monitoring.

4. The invention breaks through conventional methods of measuring resistances, effectively simplifies the measurement equipments, and can also be applied to patients with either mild or severe diseases.

5. The medical staff can remotely control the testing process through the receiving device.

6. By using absolute pressure as a basis on calculating human respiratory system parameters, errors caused by different altitudes of the test sites are greatly reduced.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. For example, specific values given herein are illustrative unless identified as being otherwise, and may be varied as a matter of design consideration. These and other variations and modifications of the embodiments disclosed herein, including of the alternatives and equivalents of the various elements of the embodiments, may be made without departing from the scope and spirit of the invention, including the invention as set forth in the following claims.

What is claimed is:

1. A human respiratory system function measuring apparatus comprising:
   a respirometer configured to receive and sense a breathing airflow of a user, and to produce a human respiratory system parameter by calculating a sensing signal,
   wherein the sensing signal includes at least an absolute pressure of the breathing airflow, wherein:
      the respirometer includes a respiration measuring pipeline;
      the absolute pressure is measured from the breathing airflow of the user in the respiration measuring pipeline with an end of the respiration measuring pipeline sealed; and
      the absolute pressure corresponds to an intrapulmonary pressure of the user,
   wherein the sensing signal further includes a gas flux and a breathing airflow temperature of the breathing airflow in the respiration measuring pipeline,
   wherein the human respiratory system function measuring apparatus is configured to calculate the human respiratory system parameter based on the gas flux of the breathing airflow, the breathing airflow temperature and the absolute pressure of the breathing airflow,
   and wherein:
      a gas density is calculated based on the intrapulmonary pressure and the breathing airflow temperature;
      a gas flow rate is calculated based on a pressure difference;
      a gas volume is calculated based on the gas flux;
      the gas flux is calculated based on the intrapulmonary pressure, the breathing airflow temperature, and the gas flow rate;
      a vital capacity is calculated based on the gas volume, and a potential energy of a maximum intrapulmonary pressure, measured at a time the user starts to exhale after fully inhaling, is calculated based on the intrapulmonary pressure and the vital capacity, wherein the potential energy is the product of the intrapulmonary pressure and the vital capacity;
      a kinetic energy of the exhaled gas converted from the entire potential energy after all gas has been exhaled is calculated based on the gas density and the gas flow rate, wherein the kinetic energy is calculated as: $Qv=\rho \times v^2/2$, wherein $Qv$ represents the kinetic energy, $\rho$ represents the gas density, and $v$ represents the gas flow rate;
      an airway resistance indicator representing an airway resistance is calculated based on the potential energy and the kinetic energy, wherein the airway resistance indicator indicates the patency in the respiratory tract while breathing and wherein the airway resistance indicator is calculated by dividing the absolute value of the difference of the potential energy and the kinetic energy by the potential energy: $|Vs-Qv|/Vs$, wherein $Vs$ represents the potential energy and $Qv$ represents the kinetic energy; and
      the loss of the kinetic energy is calculated based on the potential energy and the kinetic energy, wherein the equation of the loss is $Qz=Vs-Qv$, and $Qz$ represents the loss of the kinetic energy.

2. The human respiratory system function measuring apparatus as claimed in claim 1, wherein the respirometer is configured to calculate the gas flux from the intrapulmonary pressure, the breathing airflow temperature, and the gas flow rate, and wherein the respirometer is configured to measure a pressure difference generated by the breathing airflow, and to calculate the gas flow rate from the pressure difference.

3. The human respiratory system function measuring apparatus as claimed in claim 1, wherein the respirometer further comprises a sensor and a signal processing chip connected to the sensor, wherein:
   the sensor is configured to measure the breathing airflow of the user in the respiration measuring pipeline, and to output the sensing signal to the signal processing chip according to the measured result;
   the signal processing chip is configured to calculate the human respiratory system parameter based on the sensing signal;
   the signal processing chip is configured to output the human respiratory system parameter to a receiving device connected to a database, wherein the database comprises a clinical data; and
   the receiving device is configured to run statistics or analysis on the human respiratory system parameter utilizing the clinical data.

4. The human respiratory system function measuring apparatus as claimed in claim 3, further comprising an additional measuring device including a three-way valve, an air pipeline, a respiratory measurement gas pipeline, a measuring pipeline, and a control valve, wherein the three-way valve includes three outlet ports communicating with each other, each of the outlet ports respectively connected to the air pipeline, the respiratory measurement gas pipeline of the additional measuring device, and the measuring pipeline of the additional measuring device, wherein:
   the three-way valve comprises a valve block controlling the communication manner among the air pipeline, the respiratory measurement gas pipeline of the additional measuring device, and the measuring pipeline of the additional measuring device, and
   the air pipeline and the respiratory measurement gas pipeline of the additional measuring device are connected with the control valve, and whether the air pipeline and the respiratory measurement gas pipeline of the additional measuring device communicate with the outer environment depends on the open or closed state of the control valve.

5. The human respiratory system function measuring apparatus as claimed in claim 4, wherein the receiving device is configured to output a control signal to the signal processing chip, and the signal processing chip is configured to control the position of the valve block or the opened or closed state of the control valve.

6. The human respiratory system function measuring apparatus as claimed in claim 5, wherein the receiving device utilizes a human respiratory system parameter from the clinical data as a default threshold, and is configured to output a warning signal if the human respiratory system parameter produced by the respirometer exceeds the threshold.

7. The human respiratory system function measuring apparatus as claimed in claim 6, wherein the respiratory measurement gas pipeline of the additional measuring device is connected with a steel cylinder, and the respiratory measurement gas pipeline of the additional measuring device comprises a gas analyzing module, wherein:
   by connecting the control valve and the steel cylinder, the control valve is configured to control a respiratory measurement gas inside the steel cylinder to be outputted to the respiratory measurement gas pipeline of the additional measuring device; and
   the gas analyzing module analyzes the gas density and the composition of the respiratory measurement gas in the respiratory measurement gas pipeline of the additional measuring device.

8. The human respiratory system function measuring apparatus as claimed in claim 7, wherein the respiratory measurement gas pipeline of the additional measuring device is connected with an air bag, and while the control valve is in the opened state, the steel cylinder, the respiratory measurement gas pipeline of the additional measuring device, and the air bag all communicate with each other.

9. The human respiratory system function measuring apparatus as claimed in claim 8, further comprising a respiratory mask connected to the respirometer, the respiratory mask comprising a mask and a connecting port, the profile of the mask corresponding to the shape of the mouth and the nose on a human face, the connecting port penetrating through the mask, and the respirometer connected to the respiratory mask through the connecting port.

10. The human respiratory system function measuring apparatus as claimed in claim 9, wherein the respiratory mask comprises a filter membrane and a membrane tightening ring, wherein the appearance of the filter membrane corresponds to a cross-section of the concave surface of the mask, and wherein the membrane tightening ring is detachably assembled with the mask, with the filter membrane fixed between the membrane tightening ring and the mask.

11. The human respiratory system function measuring apparatus as claimed in claim 10, wherein the respirometer further comprises a flow-controlling device, and wherein said sensor is configured to measure the pressure difference and the breathing airflow temperature in the respiration measuring pipeline through the flow-controlling device, wherein:
   the flow-controlling device is disposed in the respiration measuring pipeline and comprises a constricted section, with the inner diameter of the constricted section smaller than the inner diameter of a free end of the flow-controlling device, so that the pressure difference is formed while gas passes therethrough, and wherein the sensor is configured to measure the pressure difference formed in the respiratory measuring pipeline caused by the flow-controlling device.

12. The human respiratory system function measuring apparatus as claimed in claim 1, further comprising a nasal respiratory assisting kit assembled with the respirometer, a free end of the nasal respiratory assisting kit having a splitter, with a profile of the splitter corresponding to the width and depth of a human nostril.

13. The human respiratory system function measuring apparatus as claimed in claim 12, further comprising a cover, wherein:
   the cover is a mouth cover connected with the respirometer; or
   the cover is a nasal cover connected with the nasal respiratory assisting kit, wherein the nasal cover corresponds to the width and depth of the human nostril.

* * * * *